(12) United States Patent
Gesotti

(10) Patent No.: US 6,788,976 B2
(45) Date of Patent: Sep. 7, 2004

(54) MOVEMENT TIMING SIMULATOR

(75) Inventor: Phil E. Gesotti, Manassas, VA (US)

(73) Assignee: Lockheed Martin Corporation, Bethesda, MD (US)

(*) Notice: Subject to any disclaimer, the term of this patent is extended or adjusted under 35 U.S.C. 154(b) by 206 days.

(21) Appl. No.: 10/005,458

(22) Filed: Nov. 2, 2001

(65) Prior Publication Data

US 2003/0088294 A1 May 8, 2003

(51) Int. Cl.$^7$ .................................. A61N 1/08
(52) U.S. Cl. ........................ 607/49; 340/573.1
(58) Field of Search ................ 607/48, 49, 77, 607/45, 46; 340/573.1; 600/557–559

(56) References Cited

U.S. PATENT DOCUMENTS

| | | |
|---|---|---|
| 4,165,750 A | 8/1979 | Aleev et al. |
| 4,340,063 A | 7/1982 | Maurer |
| 4,580,339 A | 4/1986 | Ioffe |
| 4,669,480 A | 6/1987 | Hoffman |
| 4,697,808 A | 10/1987 | Larson et al. |
| 4,754,759 A | 7/1988 | Allocca |
| 4,759,368 A | 7/1988 | Spanton et al. |
| 4,769,881 A | 9/1988 | Pedigo |
| 4,917,092 A | 4/1990 | Todd et al. |
| 4,922,908 A | 5/1990 | Morawetz et al. |
| 4,989,605 A | 2/1991 | Rossen |
| 5,038,797 A | 8/1991 | Batters |
| 5,121,747 A | 6/1992 | Andrews |
| 5,184,617 A | 2/1993 | Harris et al. |
| 5,330,515 A | 7/1994 | Rutecki et al. |
| 5,330,527 A | 7/1994 | Montecalvo et al. |
| 5,350,414 A | 9/1994 | Kolen |
| 5,562,707 A | 10/1996 | Prochazka et al. |
| 5,597,309 A | 1/1997 | Riess |
| 5,814,093 A | 9/1998 | Stein |
| 5,895,416 A | 4/1999 | Barreras, Sr. et al. |
| 5,961,542 A | 10/1999 | Agarwala |
| 5,964,789 A | 10/1999 | Karsdon |

(List continued on next page.)

FOREIGN PATENT DOCUMENTS

| | | |
|---|---|---|
| EP | 0 911 061 | 4/1999 |
| WO | WO 90/12293 | 10/1990 |
| WO | WO 97/39795 | 10/1997 |
| WO | WO 97/39796 | 10/1997 |

OTHER PUBLICATIONS

Choi et al. "Selectivity of Multiple–Contact Nerve Cuff Electrodes: A Simulation Analysis," *IEEE Transactions of Biomedical Engineering*, vol. 48, No. 2, pp. 165–172 (Feb., 2001).

Popovic et al. "Surface–Stimulation Technology for Grasping and Walking Neuroprostheses," *IEEE Engineering in Medicine and Biology* pp. 82–93 (Jan./Feb., 2001).

Riess et al., "Augmented Reality and Parkinson's Disease," (2 pgs.) http://www.ftp.hitl.washington.edu/publications/r–99–5/ (Jan. 22, 2002).

*Primary Examiner*—Jeffrey R. Jastrzab
(74) *Attorney, Agent, or Firm*—Fogg & Associates LLC

(57) ABSTRACT

Movement timing stimulators that aid in the relief of the symptoms of neurological movement disorders are provided. In one embodiment, a movement stimulator has a control unit. A stimulator is coupled to an output of the control unit. The stimulator is adapted to provide stimulation to an area of the body of a living subject. A sensor is also coupled to the control unit and is adapted to be disposed external to the body. The sensor is adapted to respond to a physical stimulus and to provide input to the control unit. The stimulator adapts to this physical stimulus to selectively provide at least one of a dual-polarity signal for providing cutaneous stimulation, a phased signal for providing surround sound aural stimulation, and a signal for providing visual stimulation transmitted to the stimulator by the control unit.

51 Claims, 10 Drawing Sheets

U.S. PATENT DOCUMENTS

| | | |
|---|---|---|
| 5,983,140 A * | 11/1999 | Smith et al. .................. 607/59 |
| 6,016,449 A | 1/2000 | Fischell et al. |
| 6,044,303 A | 3/2000 | Agarwala et al. |
| 6,066,163 A | 5/2000 | John |
| 6,083,156 A | 7/2000 | Lisiecki |
| 6,094,598 A | 7/2000 | Elsberry et al. |
| 6,246,912 B1 | 6/2001 | Sluijter et al. |
| 6,356,784 B1 | 3/2002 | Lozano et al. |
| 6,424,868 B1 * | 7/2002 | Smith et al. .................. 607/59 |

* cited by examiner

MOVEMENT TIMING SIMULATOR

CROSS REFERENCE TO RELATED APPLICATIONS

This application is related to copending application U.S. Ser. No. 09/659,351, entitled *Adaptive Stimulator for Relief of Symptoms of Neurological Disorders*, filed on Sep. 12, 2000, which application is incorporated herein by reference.

TECHNICAL FIELD

The present invention relates generally to the field of electronics and, in particular, to movement timing stimulators.

BACKGROUND

Neurological movement disorders, such as Parkinson's disease, neuropathy, cerebellar degeneration, etc. include symptoms that affect the ability to properly control and time coordinated movement. Many neurological movement disorders involve the loss of sensing function or inability to process sensing information. This often makes it difficult for an afflicted individual to sense, for example, head position, stooped posture, limb position, such as leg position making walking difficult, etc. Many neurological movement disorders have no cure at present, only treatments to temporarily relieve the various symptoms. For example, medications can be used to temporarily restore the loss of sensing function or inability to process sensing information. However, the effectiveness of many of these medications often varies substantially from patient to patient. Moreover, some medications have undesirable side effects.

For the reasons stated above, and for other reasons stated below which will become apparent to those skilled in the art upon reading and understanding the present specification, there is a need in the art for improvements in techniques to provide patients affected with neurological movement disorders relief from the symptoms.

SUMMARY

The above-mentioned problems with treatment of the symptoms of neurological movement disorders and other problems are addressed by embodiments of the present invention and will be understood by reading and studying the following specification. Embodiments of the present invention provide movement-timing stimulators that aid in the relief of the symptoms of neurological movement disorders by providing sensing and stimulation at various locations of the body of a living subject.

In one embodiment, a movement timing stimulator is provided. The movement stimulator has a control unit. A stimulator is coupled to an output of the control unit. The stimulator is adapted to provide stimulation to an area of the body of a living subject. A sensor is also coupled to the control unit and is adapted to be disposed external to the body. The sensor is adapted to respond to a physical stimulus and to provide input to the control unit. The stimulator is adapted to selectively provide at least one of a dual-polarity signal for providing cutaneous stimulation, a phased signal for providing surround sound aural stimulation, and a signal for providing visual stimulation transmitted to the stimulator by the control unit.

In another embodiment, a movement timing stimulator having a wristband and an elbow-band is provided. A first stimulation electrode is disposed on an interior of the wristband for cutaneous stimulation of a wrist area of a user. A second stimulation electrode is disposed on an interior of the elbow-band for cutaneous stimulation of an elbow area of the user. A control unit is secured to the wristband and an output of the control unit is electrically connected to the first and second stimulation electrodes. A sensor is electrically connected to the control unit and is adapted to be disposed external to the body. The sensor is adapted to respond to a physical stimulus and provide input to the control unit. The first and second stimulation electrodes are adapted to selectively provide cutaneous stimulation in response to the sensor input to the control unit.

In yet another embodiment, a movement timing stimulator having an ankle-band and a knee-band is provided. A first stimulation electrode is disposed on an interior of the ankle-band for cutaneous stimulation of an ankle area of a user. A second stimulation electrode disposed on an interior of the knee-band for cutaneous stimulation of a knee area of the user. A control unit is secured to the ankle-band and an output of the control unit is electrically connected to the first and second stimulation electrodes. A sensor is electrically connected to the control unit and is adapted to be disposed external to the body. The sensor is adapted to respond to a physical stimulus and provide input to the control unit. The first and second stimulation electrodes are adapted to selectively provide cutaneous stimulation in response to the sensor input to the control unit.

Other embodiments are described and claimed.

DETAILED DESCRIPTION

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense.

Figure 1:
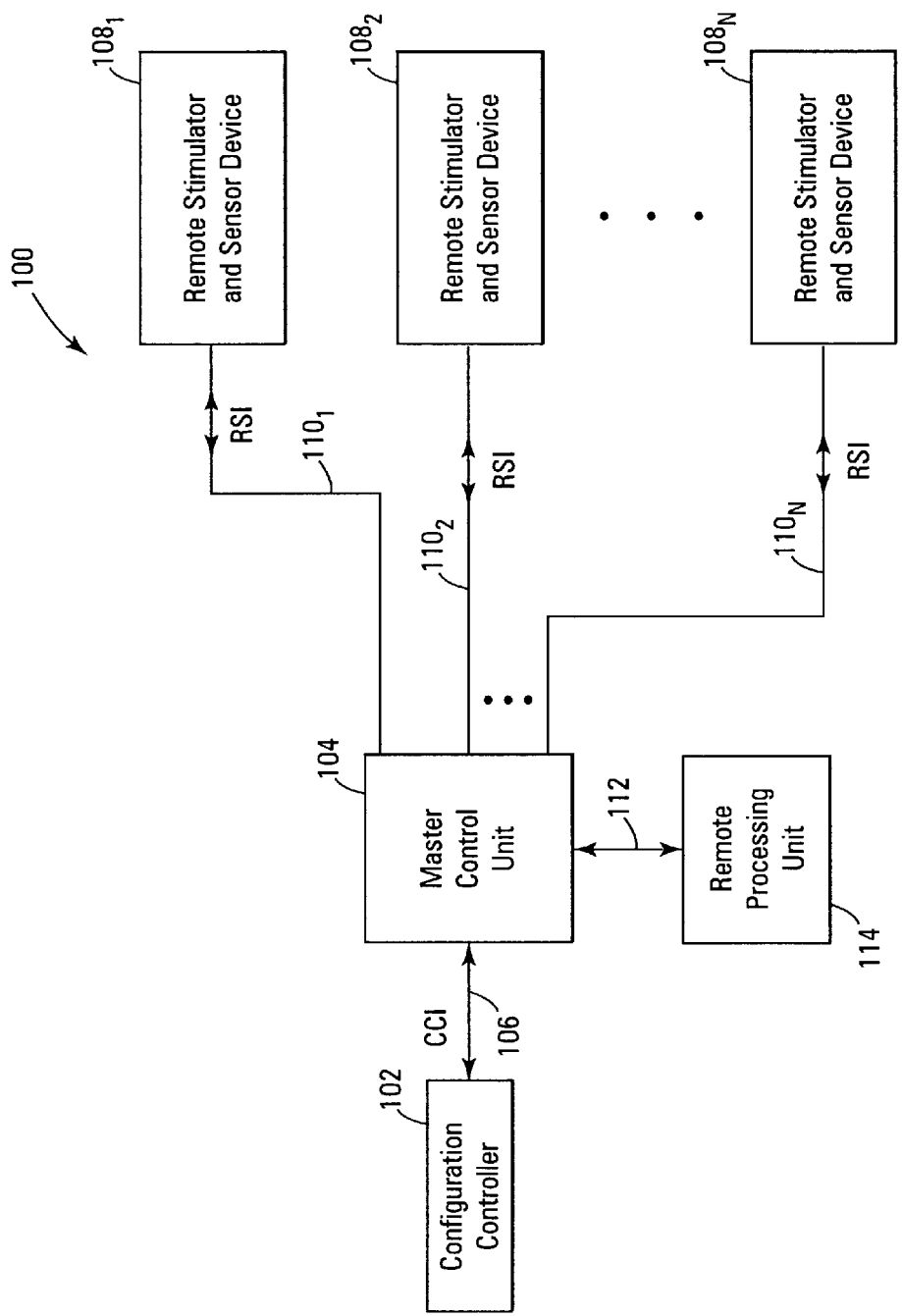
FIG. 1 is a block diagram of an embodiment of a movement timing stimulator according to the teachings of the present invention.

FIG. 1 is a block diagram of an embodiment of a movement timing stimulator 100 according to the teachings of the present invention. Movement timing stimulator 100 has a configuration controller 102, e.g., a wearable computer, such as a personal digital assistant, communicatively coupled to a master control unit 104 by a configuration control interface (CCI) 106. In one embodiment, configuration control interface 106 is a wireless interface, e.g., Infrared Data Association (IrDA) or BLUETOOTH, a hard-wire interface, such as RS-232, asynchronous serial port, Universal Serial Bus, or the like. Configuration controller 102 is used to program master control unit 104. Master control unit 104 is communicatively coupled to each of remote stimulator and sensor devices $108_1$ to $108_N$ by remote stimulation interfaces (RSIs) $110_1$ to $110_N$, respectively. In one embodiment, each of remote stimulation interfaces $110_1$ to $110_N$, is implemented as one or more of a wireless connection, e.g., IrDA or BLUETOOTH, as a bi-directional cable, or the like.

Figure 4:
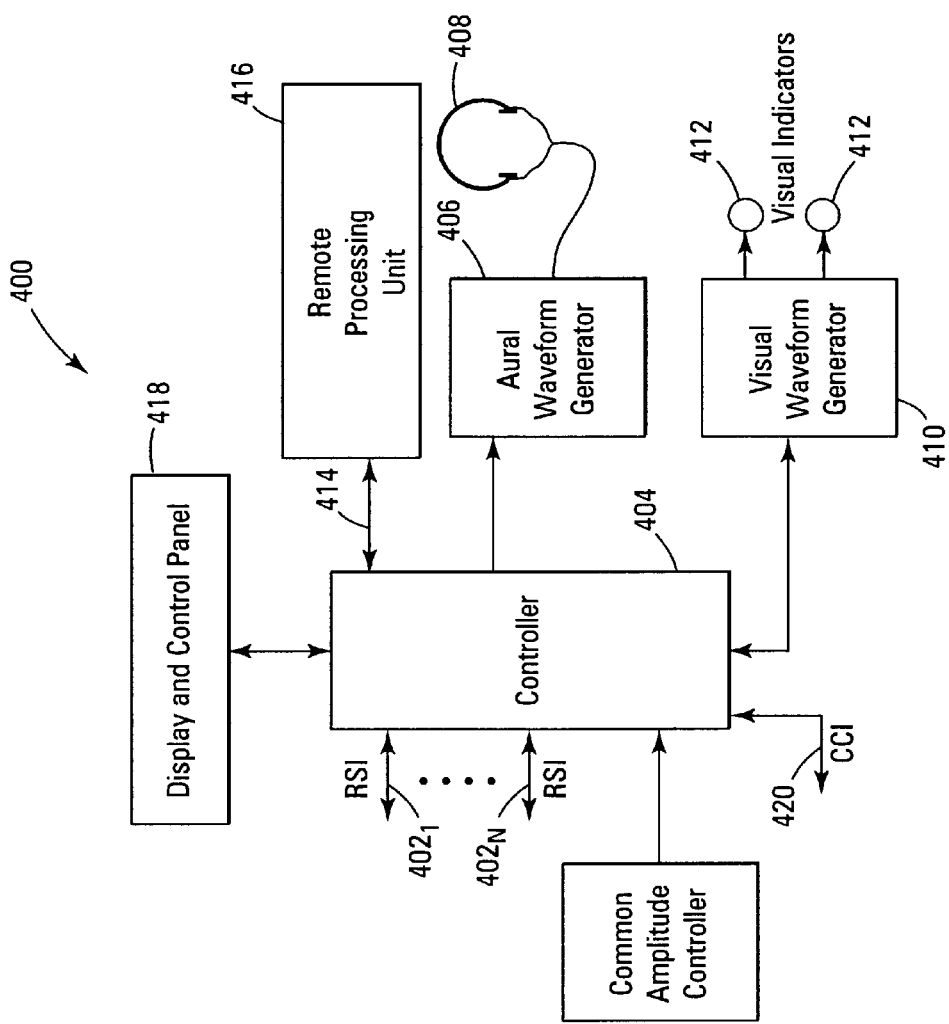
FIG. 4 is a block diagram of an embodiment of a master control unit of an embodiment of a movement timing stimulator according to the teachings of the present invention.

Master control unit 104 controls each of remote stimulator and sensor devices $108_1$ to $108_N$ as programmed by configuration controller 102. In one embodiment, master control unit 104 is as described below and as illustrated in FIG. 4. Each of remote stimulator and sensor devices $108_1$ to $108_N$ selectively receives sensory signals, e.g., indicative of a position and/or motion of the human body, and transmits the sensory signals to master control unit 104. Master control unit 104 selectively instructs each of remote stimulator and sensor devices $108_1$ to $108_N$ to selectively transmit stimulation signals for stimulating portions of the human body based on the sensory signals.

In one embodiment, configuration controller 102 is selectively communicatively coupled to remote stimulator and sensor devices $108_1$ to $108_N$ on an individual basis. In another embodiment, an encoded wireless link 112, e.g., IrDA, BLUETOOTH, or the like, selectively communicatively couples master control unit to a remote processing unit 114, such as a personal computer or a personal data assistant. In one embodiment, encoded wireless link 112 and remote processing unit 114 are respectively as described below for encoded wireless link 414 and remote processing unit 416 of FIG. 4.

Figure 2:
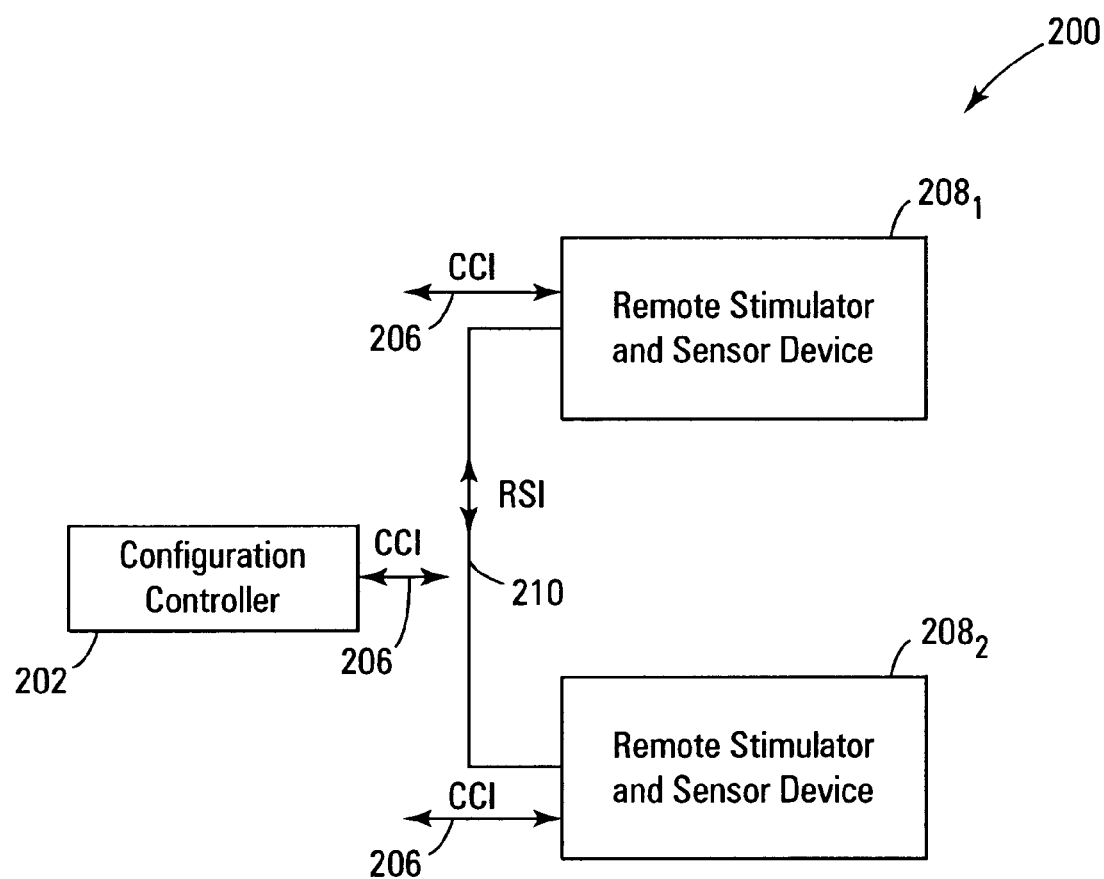
FIG. 2 is a block diagram of another embodiment of a movement timing stimulator according to the teachings of the present invention.

FIG. 2 is a block diagram of an embodiment of a movement timing stimulator 200 according to the teachings of the present invention. Movement timing stimulator 200 has a configuration controller 202 selectively communicatively coupled to each of remote stimulator and sensor devices $208_1$ to $208_2$. Remote stimulator and sensor devices $208_1$ to $208_2$ are communicatively intercoupled by a remote stimulation interface (RSI) 210. In one embodiment, configuration control interface 206 and remote stimulation interface 210 are respectively as described above for configuration control interface 106 and remote stimulation interfaces $110_1$ to $110_N$.

Configuration controller 202 is used to selectively program each of remote stimulator and sensor devices $208_1$ to $208_2$. In operation, one of remote stimulator and sensor devices $208_1$ to $208_2$ is selected as a master controller, e.g., using an arbitration scheme, for controlling both remote stimulator and sensor devices $208_1$ to $208_2$. In one embodiment, the arbitration scheme involves selecting as the master controller the first of remote stimulator and sensor devices $208_1$ to $208_2$ that transmits a control signal to the other of remote stimulator and sensor devices $208_1$ to $208_2$ via remote stimulation interface 210. When both remote stimulator and sensor devices $208_1$ to $208_2$ try to transmit control signals to each other at the same time, causing the respective control signals to collide, one of remote stimulator and sensor devices $208_1$ to $208_2$ is randomly selected as the master controller.

Each of remote stimulator and sensor devices $208_1$ and $208_2$ selectively receives a sensory signal indicative of a position and/or motion of the human body. The one of remote stimulator and sensor devices $208_1$ and $208_2$ not selected as the master controller transmits its sensory signal to the one of remote stimulator and sensor devices $2081$ and $208_2$ selected as the master controller. The one of remote stimulator and sensor devices $208_1$ and $208_2$ selected as the master controller selectively instructs each of remote stimulator and sensor devices $208_1$ and $208_2$ to selectively transmit signals for stimulating portions of the human body based on the respective sensory signals.

Figure 3:
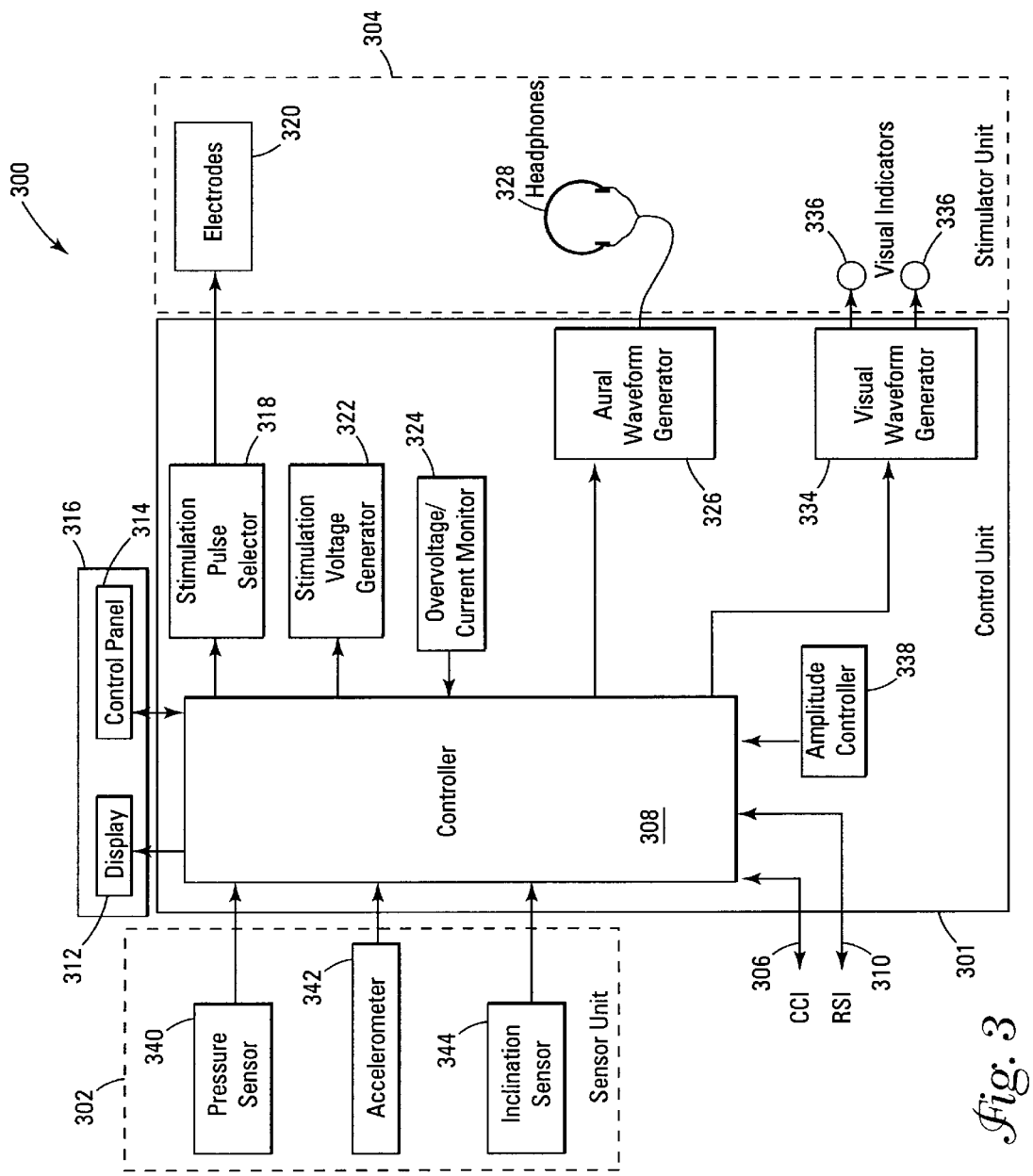
FIG. 3 is a block diagram of an embodiment of a remote stimulator and sensor device of an embodiment of a movement timing stimulator according to the teachings of the present invention.

FIG. 3 is a block diagram of an embodiment of remote stimulator and sensor device 300. In one embodiment, remote stimulator and sensor device 300 is a stand-alone device and functions as a movement timing stimulator having a single remote stimulator and sensor device.

Remote stimulator and sensor device 300 includes a control unit 301 connected to a sensor unit 302 and a stimulator unit 304. Sensor unit 302 is responsive to physical stimuli, such as pressure, acceleration, and/or inclination, and stimulation unit 304 provides stimuli, such as aural, visual, and/or cutaneous to the human body. Control unit 301 interrogates sensor unit 302 and receives sensory data. Control unit 301 determines if the sensory data meets a certain threshold or criteria. When the sensory data meets or exceeds the determined threshold, control unit 301 generates stimulation signals and transmits the signals to stimulator unit 304, e.g., electrodes 320, headphones 328, and/or visual indicators 336, as appropriate.

In one embodiment, each of electrodes 320 is attached to the skin at a strategic location on the human body for providing cutaneous stimulation. In another embodiment, one of electrodes 320 is a common return electrode and the others are stimulation electrodes. The common return electrode is in direct contact with the skin and provides a return path for each of the stimulation electrodes attached to the skin. The common return electrode provides a large surface, and as a result a lower impedance, than each of the stimulation electrodes. This helps to keep the current at the contact location at a comfortable level for the patient.

In one embodiment, sensor unit 302 includes a pressure sensor 340, an accelerometer 342, e.g., a three axis accelerometer, and/or an inclination sensor 344. Therefore, the sensory data includes pressure data, acceleration data, and/or inclination data. These sensors are used at different locations on the human body for providing sensory data for those locations. In one embodiment, accelerometer 342 is disposed on a patient's wrist for sensing arm motion, on a patient's ankle for sensing leg motion, or the like. In another embodiment, pressure sensor 340 is disposed on a foot of a patient for sensing whether or not the patient is exerting a force on that foot. In one embodiment, inclination sensor 344 is attached to a patient's head, e.g., for sensing a drooping or tilted head. In one embodiment, accelerometer 342 is integral with remote stimulator and sensor device 300.

Control unit 301 includes a controller 308 that receives sensory data from sensor unit 302 and transmits instructions to stimulator unit 304. Controller 308 includes software that includes algorithms for processing the information from input signals, such as an operator control signal, a signals from stimulator unit 304 indicative of a physical stimulus, or the like, and determines the response(s) required to produce simulation and stimulation. Controller 308 generates the basic timing for stimulation waveforms that are transmitted to stimulation unit 304. Controller 308 also adjusts frequency, pulse-width, waveform shape, and amplitude based on information received from sensor unit 302.

In one embodiment, information for setting the basic timing for stimulation waveforms and/or for programming various frequencies, pulse-widths, amplitudes, waveform shapes, etc. in controller 308 is transmitted to controller 308 via remote stimulation interface 310. In another embodiment, remote stimulation interface 310 includes remote stimulation interfaces, such as remote stimulation interfaces $110_1$ to $110_N$ of FIG. 1, of movement timing stimulator 100 and thus the information is received from master controller, such as master controller 102 of FIG. 1.

In other embodiments, remote stimulation interface 310 includes a remote stimulation interface 210 of movement timing stimulator 200, as described with respect to FIG. 2. In these embodiments, the information is transmitted from the controller, such as controller 308, of the one of remote stimulator and sensor devices $208_1$ and $208_2$ selected as the master controller via remote stimulation interface 210 to the controller of the other of remote stimulator and sensor devices $208_1$ and $208_2$.

In one embodiment, information for setting the basic timing for stimulation waveforms and/or for programming various frequencies, pulse-widths, amplitudes, waveform shapes, etc. in controller 308 is transmitted to controller 308 via a configuration control interface (CCI) 306. In another embodiment, configuration control interface 306 includes configuration control interface 206 of movement timing stimulator 200.

In other embodiments, remote stimulator and sensor device 300 includes a display 312 connected to controller 308. In one embodiment, remote stimulator and sensor device 300 includes a control panel 314 connected to controller 308. In an alternate embodiment, remote stimulator and sensor device 300 includes an integrated display and control panel 316 connected controller 308. Control panel 314 and integrated control panel 316 provide an operator interface inputting information for setting the basic timing for stimulation waveforms, for programming various frequencies, pulse-widths, amplitudes, waveform shapes, etc. in controller 308, and/or for outputting data, for example, on the effectiveness of various remote stimulator and sensor devices, including the effectiveness of stimulation signals, stimulator placement, and the like.

In one embodiment, control unit 301 includes a stimulation voltage pulse generator 318 connected to electrodes 320 of stimulator unit 304. Stimulation pulse selector 318 selects individual stimulation signals for electrodes 320. In one embodiment, stimulation signals are phased, as non-overlapping pulses, to prevent unwanted cross coupling of currents between electrodes 320. In some applications, the body adapts to static waveforms, thus decreasing sensitivity to the effect of the waveforms. In one embodiment, selecting of one of a collection of dynamic waveform changes that vary amplitude, frequency, and/or pulse-width of the stimulation signals in some predetermined manner prolongs stimulation effectiveness. In another embodiment, stimulation effectiveness is prolonged using dual-polarity waveforms, e.g., alternately supplying waveforms of positive and negative polarity. This reduces charge build-up on the skin to which electrodes 320 are attached, which charge build-up is related to decreasing sensitivity.

Control unit 301 further includes a stimulation generator 322 coupled between controller 308 and stimulation pulse selector 318. Stimulation pulse selector 318 receives input from controller 308 and generates stimulation voltages for input to stimulation pulse selector 318. Control unit 301 includes an over voltage/current monitoring circuit 324 coupled between stimulation generator 322 and controller 308. Monitoring circuit 324 monitors stimulation electrode voltage and current and provides information to controller 308 to prevent exposure of the patient to uncomfortable stimulation levels.

In one embodiment, control unit 301 includes an aural waveform generator 326 connected between controller 308 and an aural stimulator, e.g., headphones 328, of stimulator unit 304. Aural waveform generator 326 receives input from controller 308 for input to headphones 328. In one embodiment, headphones 328 provide a signal for producing an aural timing cue that alternates between each of headphones 328. In another embodiment, the phase and the amplitude of the signal supplied to each individual earpiece of headphones 328 is varied to produce an aural timing cue perceived by a patient wearing headphones 328 as moving in three dimensions, such as surround sound. This provides directional orientation and a synchronizing rhythm to the patient. In one embodiment, headphones 328 provide aural cues for a drooping or tilted head and cadence for walking and repetitive activities.

In another embodiment, control unit 301 includes a visual waveform generator 334 connected between controller 308 and visual indicators 336, e.g., light sources, such as light emitting diodes, of stimulator unit 304. Visual waveform generator 334 receives input from controller 308 for input to visual indicators 336 to produce various light patterns. In one embodiment, visual indicators 336 provide timing cues synchronized with alternating patterns of cutaneous stimulation provided by electrodes 320. In another embodiment, visual indicators are attached to a user so as to be perceivable directly by the user or by the user's peripheral vision, e.g., on the wrist, in a shirt pocket, or the like.

Control unit 301 also has an amplitude controller 338 connected to controller 308. Amplitude controller 338 provides amplitude control for signals supplied to stimulator unit 304, e.g., electrodes 320, headphones 328, and/or visual indicators 336. In embodiments of movement timing stimulator 100, amplitude controller 338 is overridden allowing master control unit 104 of movement timing stimulator 100 to provide a common amplitude control, for example, to each of remote stimulator and sensor devices $108_1$ to $108_N$.

FIG. 4 illustrates an embodiment of a master control unit 400 for the synchronization and master control of several remote stimulator and sensor devices, e.g., remote stimulator and sensor devices $108_1$ to $108_N$ of movement timing stimulator 100, via remote stimulation interfaces (RSIs) $402_1$ to $402_N$. In one embodiment, remote stimulation interfaces $402_1$ to $402_N$ are as described above for remote stimulation interfaces (RSIs) $110_1$ to $110_N$ for movement timing stimulator 100.

Master control unit 400 includes a controller 404. Controller 404 generates basic timing signals and distributes these timing signals to several remote stimulator and sensor devices via remote stimulation interfaces $402_1$ to $402_N$. In one embodiment, the timing signals instruct a control unit, e.g., control unit 301 of remote stimulator and sensor device 300, when to generate and transmit stimulation signals to a stimulator unit, e.g., stimulator unit 304 of remote stimulator and sensor device 300. In another embodiment, controller 404 receives sensory signals via remote stimulation interfaces $402_1$ to $402_N$ from a control unit of a remote stimulator and sensor device, such as received at control unit 301 from sensor unit 302 of remote stimulator and sensor device 300.

In one embodiment, an aural waveform generator 406 is connected between controller 404 and headphones 408. Controller 404 varies the phase and amplitude of signals supplied to each of headphones 408 to provide a surround sound timing cue to a patient wearing headphones 408. This provides directional orientation and a synchronizing rhythm to the patient. In one embodiment, headphones 410 provide aural cues for a drooping or tilted head and cadence for walking and repetitive activities.

In another embodiment, a visual waveform generator 410 is connected between controller 404 and visual indicators 412, e.g., light emitting diodes or the like. In one embodiment, visual indicators 412 provide timing cues synchronized with alternating patterns of cutaneous stimulation provided by electrodes, e.g., electrodes 320, of several remote stimulator and sensor devices, such as remote stimulator and sensor devices $108_1$ to $108_N$.

In one embodiment, an encoded wireless link 414, such as IrDA, BLUETOOTH, or the like, selectively communicatively interconnects controller 404 to a remote processing unit 416, such as a personal computer, personal data assistant, or the like. Encoded wireless link 414 enables remote processing unit 416 to monitor the performance of several remote stimulator and sensor devices, such as remote stimulator and sensor devices $108_1$ to $108_N$ via controller 404 without impacting patient mobility. Encoded wireless link 414 enables remote processing unit 416 to adjust various parameters, e.g., threshold or criteria for the sensory signals, of a movement timing stimulator, such as movement timing stimulator 100, without patient conscious awareness. This facilitates blind studies of the effectiveness of various remote stimulator and sensor devices connected to a movement timing stimulator, including the effectiveness of stimulation signals, stimulator placement, and the like. Data transmitted to and from remote processing unit 416 via encoded wireless link 414 is encoded to reduce the risk of unauthorized recording of the data and the risk of transmitting erroneous command signals.

In one embodiment, master control unit 400 includes a display and control panel 418 coupled to controller 404. Display and control panel 418 provides an operator interface for inputting information, for setting the basic timing for stimulation waveforms, and/or for programming various frequencies, pulse-widths, amplitudes, waveform shapes, etc. in controller 404 for various remote stimulator and sensor devices. Display and control panel 418 also provides an operator interface for outputting data, for example, on the effectiveness of various remote stimulator and sensor devices, including the effectiveness of stimulation signals, stimulator placement, and the like. In one embodiment, display and control panel 418 has separate display and control panels. In another embodiment, display and control panel 418 has integrated display and control panels.

In other embodiments, information for setting the basic timing for stimulation waveforms and/or for programming various frequencies, pulse-widths, amplitudes, waveform shapes, etc. in controller 404 is transmitted to controller 404 via a configuration control interface (CCI) 420 by a configuration controller, e.g., configuration controller 102. In one embodiment, configuration control interface 420 is as described above for configuration control interface 106.

Figure 5:
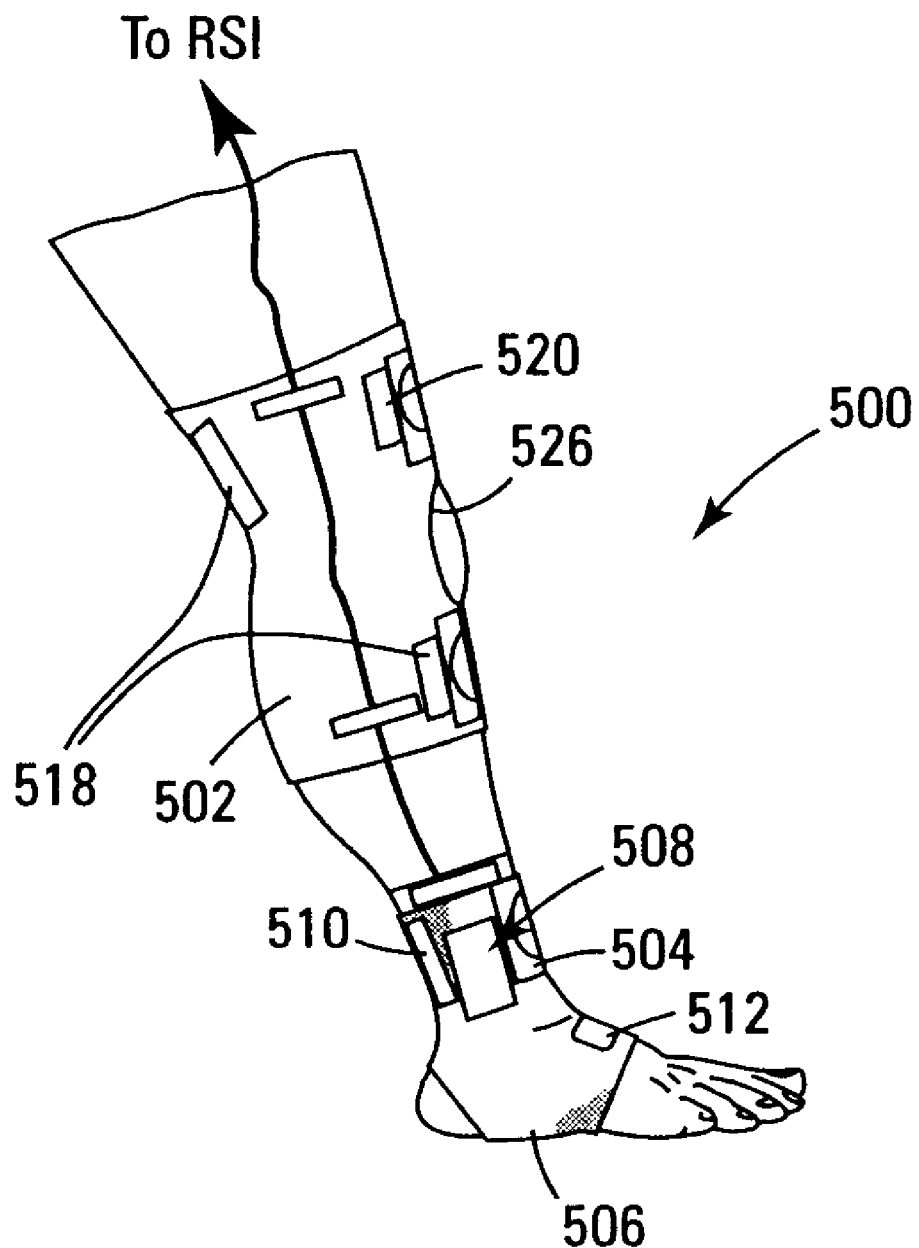
FIG. 5 illustrates an embodiment of a movement timing stimulator for leg stimulation according to the teachings of the present invention.
Figure 6:
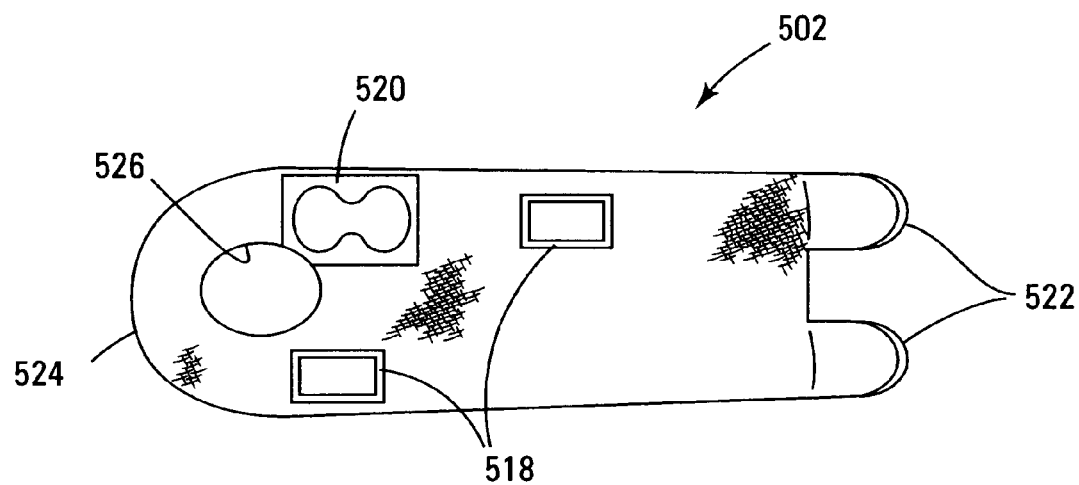
FIG. 6 is an inside view of an embodiment of a knee-band of the movement timing stimulator of FIG. 5 unwrapped.
Figure 7:
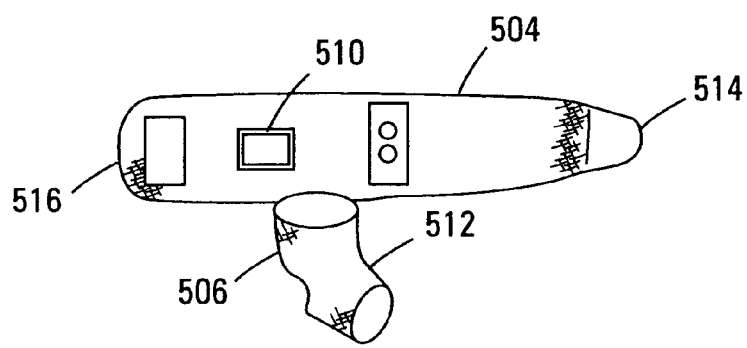
FIG. 7 is an inside view of an embodiment of an ankle-band of the movement timing stimulator of FIG. 5 unwrapped.

FIG. 5 illustrates an embodiment of a movement timing stimulator 500 for stimulating a leg of a patient. Movement timing stimulator 500 has a single remote stimulator and sensor device 508. Movement timing stimulator 500 includes a knee-band 502 adapted to be wrapped around a knee of a patient. FIG. 6 is an inside view of knee-band 502 unwrapped. Movement timing stimulator 500 also includes an ankle-band 504 adapted to be wrapped around an ankle of the patient. In one embodiment, ankle-band 504 is attached to a sock 506. FIG. 7 is an inside view of ankle-band 504 unwrapped and attached to sock 506.

Remote stimulator and sensor device 508 is securable to ankle-band 504 using snaps, straps and buckles, hook-and-loop material, such as VELCRO, placeable in a pocket on ankle-band 504, or the like. In one embodiment, remote stimulator and sensor device 508 is one of two remote stimulator and sensor devices, e.g., sensor devices $208_1$, to $208_2$, of a movement timing stimulator, e.g., movement timing stimulator 200, that intercommunicate via a remote stimulation interface (RSI), e.g., remote stimulation interface 210. In another embodiment, remote stimulator and sensor device 508 is one of several remote stimulator and sensor devices, e.g., remote stimulator and sensor devices $108_1$ to $108_N$, of a movement timing stimulator, e.g., movement timing stimulator 100, that communicates with a master control unit, e.g., master control unit 400 or master control unit 104, via a remote stimulation interface, e.g., one of remote stimulation interfaces $110_1$ to $110_N$. In other embodiments, remote stimulator and sensor device 508 is as described above for remote stimulator and sensor device 300.

Ankle-band 504 includes a stimulation electrode 510, as shown in FIGS. 5 and 7, that is selectively attachable, in one embodiment, to the interior of ankle-band 504 using snaps, straps and buckles, hook-and-loop material, such as VELCRO or the like. Sock 506 includes stimulation electrode 512, as shown in FIGS. 5 and 7, that is selectively attachable, in one embodiment, to the interior of sock 506 using hook-and-loop material, such as VELCRO or the like. In one embodiment, stimulation electrodes 510 and 512 include conductive electrolytes in the form of fluids, gels, a flexible conductive fabric or material, or the like for electrically coupling stimulation electrodes 510 and 512 to the skin adjacent the ankle and the skin at the top of the foot, respectively.

In one embodiment, sock 506 is stitched to ankle-band 504. In another embodiment, ankle-band 504 and sock 506 are of a resilient material so that ankle-band 504 and sock 506 respectively remain in contact with the ankle and foot as the patient moves the ankle and foot. The resilient material of ankle-band 504 and sock 506, in one embodiment, respectively press stimulation electrodes 510 and 512 against the skin adjacent the ankle and the skin at the top of the foot. In some embodiments, pressure exerted by the resilient material of ankle-band 504 and sock 506 helps to support the ankle and foot, respectively. Ends 514 and 516 of ankle-band 504 are selectively fastenable to each other using hook-and-loop material, such as VELCRO, straps and buckles, snaps, or the like, for securing ankle-band 504 around the ankle.

In one embodiment, knee-band 502 includes stimulation electrodes 518 and a common return electrode 520, as shown in FIGS. 5 and 6. Stimulation electrodes 518 and common return electrode 520 are selectively attachable, in one embodiment, to the interior of knee-band 502 using hook-and-loop material, such as VELCRO or the like. In some embodiments, stimulation electrodes 518 and common return electrode 520 include conductive electrolytes in the form of fluids, gels, a flexible conductive fabric or material, or the like for electrically coupling stimulation electrodes 518 and common return electrode 520 to the skin adjacent the knee.

In another embodiment, knee-band 502 is of a resilient material so that knee-band 502 remains in contact with the skin adjacent the knee as the patient moves. The resilient material of knee-band 502, in one embodiment, presses stimulation electrodes 518 and common return electrode 520 against the skin adjacent the knee. In some embodiments, pressure exerted by the resilient material of knee-band 502 helps to support the knee. Ends 522 and 524 of knee-band 502 are selectively fastenable to each other using hook-and-loop material, such as VELCRO, straps and buckles, snaps, or the like, for securing knee-band 502 around a knee. In one embodiment, knee-band 502 includes an aperture 526 for receiving the knee, as shown in FIG. 5.

Common return electrode 520 provides the return path for each of stimulation electrodes 510, 512, and 518. Common return electrode 520 provides a large surface in contact with the skin. This helps to keep the current density at the contact surface of common return electrode 520 at a comfortable level for the patient. Each of stimulation electrodes 510, 512, and 518 and common return electrode 520 are connected to remote stimulator and sensor device 508. In one embodiment, remote stimulator and sensor device 508 includes an integral accelerometer, e.g., a three-axis accelerometer, configurable to provide information to remote stimulator and sensor device 508 on leg motion and/or to support adaptive modification of stimulation signals supplied to stimulation electrodes 510, 512, and 518. In one example, stimulation electrodes 510, 512, and 518 and common return electrode 520 are as described in copending application U.S. Ser. No. 09/659,351, entitled *Adaptive Stimulator for Relief of Symptoms of Neurological Disorders*, filed on Sep. 12, 2000.

Figure 8:
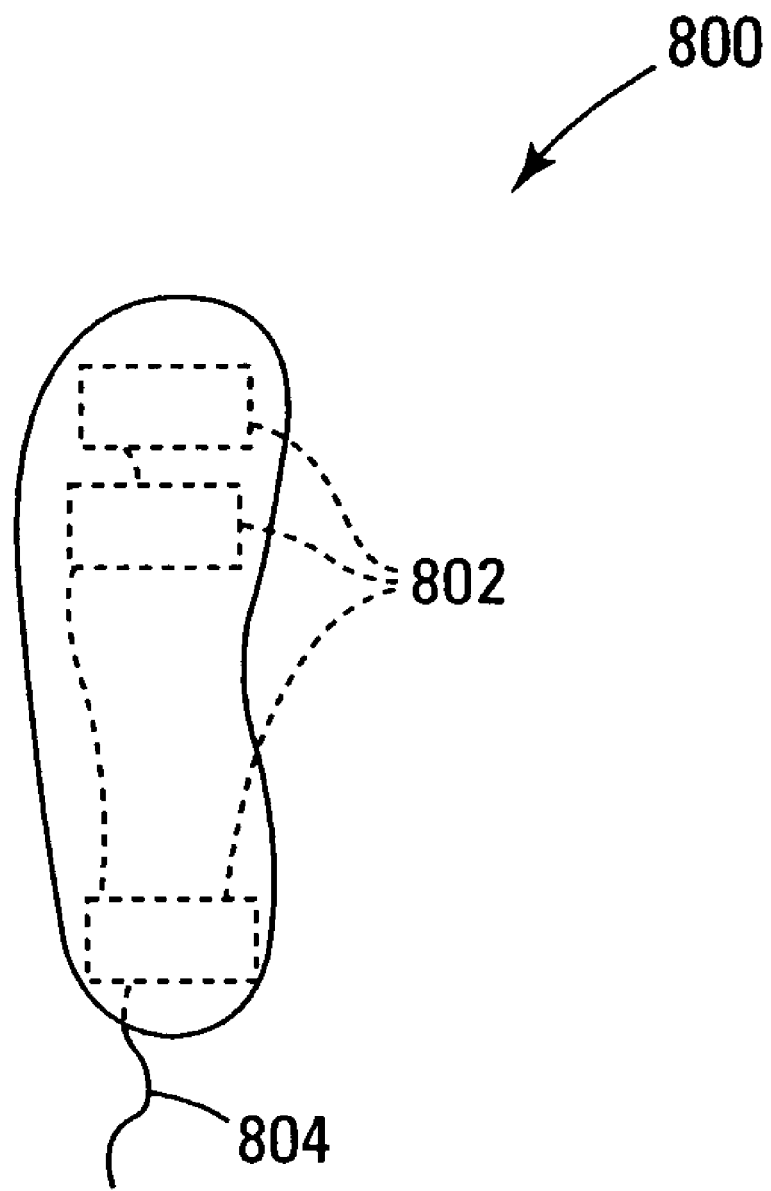
FIG. 8 illustrates an embodiment of a pressure sensing shoe insert according to the teachings of the present invention.

In one embodiment, pressure sensors 802 disposed on a shoe insert 800, as shown in FIG. 8, are coupled to a remote stimulator and sensor device, such as remote stimulator and sensor device 508, by a lead wire 804. In one example, shoe insert comprises the shoe insert and sock insert of copending application U.S. Ser. No. 09/659,351, entitled *Adaptive Stimulator for Relief of Symptoms of Neurological Disorders*, filed on Sep. 12, 2000.

Shoe insert 800 transmits data to a remote stimulator and sensor device on the motion and active function of a foot. In one embodiment, a gait, e.g., the walking action of the foot is compared, e.g., at a remote stimulator and sensor device or master controller, such as master controller 100 or 400, to a normal gait where there is typically a heel, ball of foot, heel sequence. The master controller or remote stimulator and sensor device, in one embodiment, modifies stimulation provided by stimulation electrodes, such as stimulation electrodes 510, 512, and 518, to emphasize a normal versus, for example, a flat-footed gait.

Figure 9:
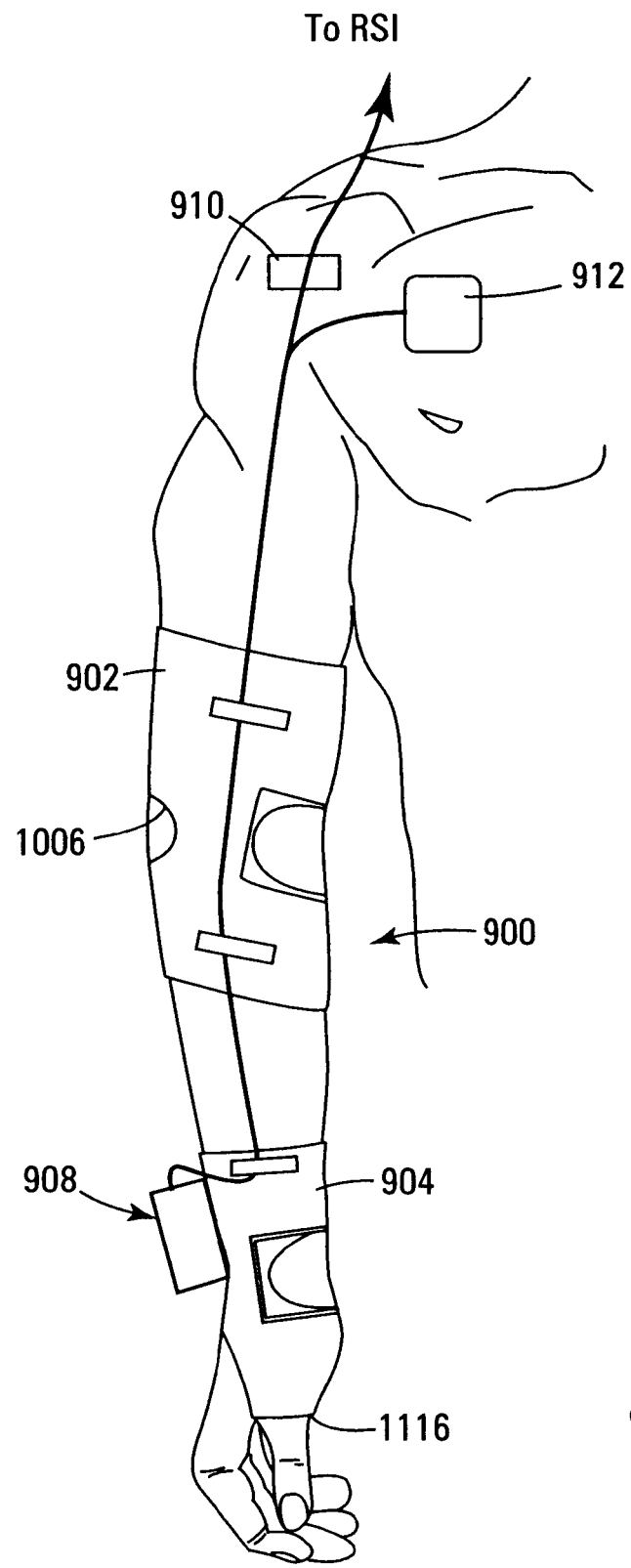
FIG. 9 illustrates an embodiment of a movement timing stimulator for arm stimulation according to the teachings of the present invention.
Figure 10:
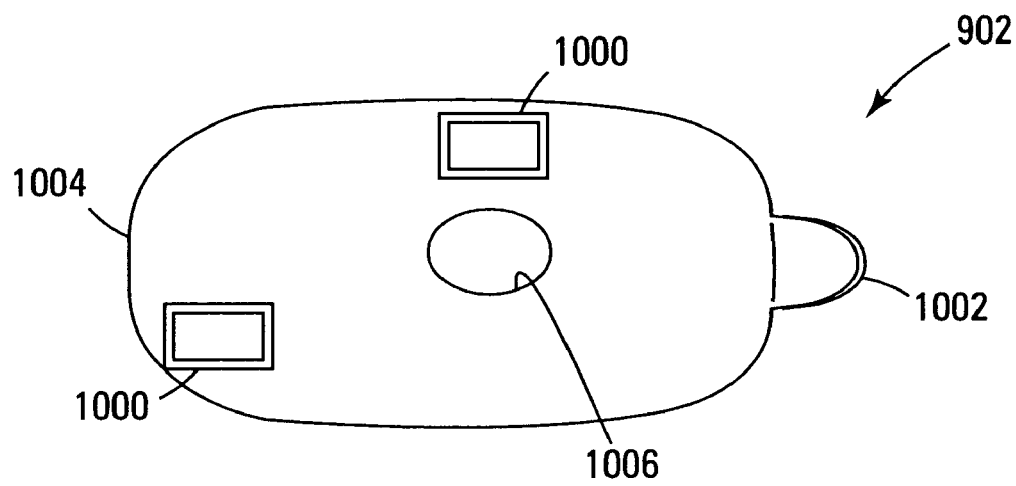
FIG. 10 is an inside view of an embodiment of an elbow-band of the movement timing stimulator of FIG. 9 unwrapped.
Figure 11:
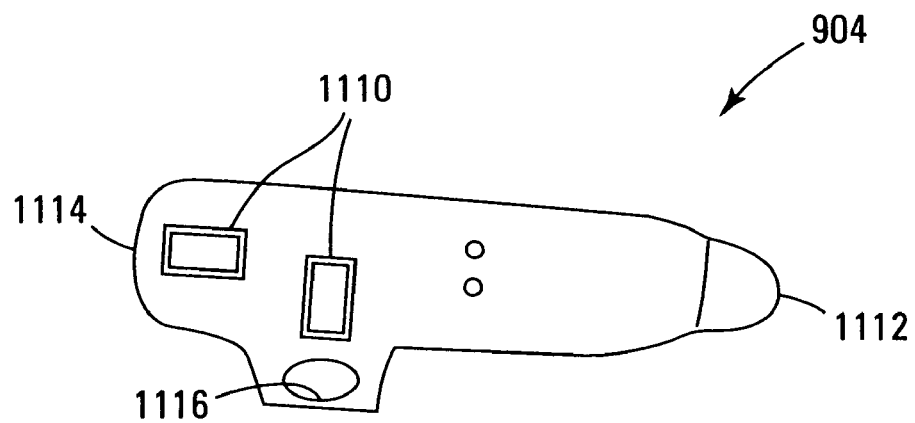
FIG. 11 is an inside view of an embodiment of a wristband of the movement timing stimulator of FIG. 9 unwrapped.

FIG. 9 illustrates an embodiment of a movement timing stimulator 900 for stimulating an arm of a patient. Movement timing stimulator 900 has a single remote stimulator and sensor device 908. Movement timing stimulator 900 includes an elbow-band 902 adapted to be wrapped around an elbow of a patient. FIG. 10 is an inside view of elbow-band 902 unwrapped. Movement timing stimulator 900 also includes a wristband 904 adapted to be wrapped around a wrist of the patient. FIG. 11 is an inside view of wristband 904 unwrapped.

Remote stimulator and sensor device 908 is securable to wristband 904 using snaps, straps and buckles, hook-and-loop material, such as VELCRO, placeable in a pocket on wristband 904, or the like. In one embodiment, remote stimulator and sensor device 908 is one of two remote stimulator and sensor devices, e.g., sensor devices $208_1$ to $208_2$, of a movement timing stimulator, e.g., movement timing stimulator 200, that intercommunicate via a remote stimulation interface (RSI), e.g., remote stimulation interface 210. In another embodiment, remote stimulator and sensor device 908 intercommunicates with remote stimulator and sensor device 508. In other embodiments, remote stimulator and sensor device 908 is one of several remote stimulator and sensor devices, e.g., remote stimulator and sensor devices $108_1$ to $108_N$, of a movement timing stimulator, e.g., movement timing stimulator 100, that communicates with a master control unit, e.g., master control unit 400 or master control unit 104, via a remote stimulation interface, e.g., one of remote stimulation interfaces $110_1$ to $110_N$. In one embodiment, remote stimulator and sensor device 908 is as described above for remote stimulator and sensor device 300.

Wristband 904 includes stimulation electrodes 1110, as shown in FIG. 11, that are selectively attachable, in one embodiment, to the interior of wristband 904 using snaps, straps and buckles, hook-and-loop material, such as VELCRO or the like. In one embodiment, stimulation electrodes 1110 include conductive electrolytes in the form of fluids, gels, a flexible conductive fabric or material, or the like for electrically coupling stimulation electrodes 1110 to the skin of the wrist and the skin adjacent the thumb for stimulating the wrist and the thumb.

In one embodiment, wristband 904 is of a resilient material so that wristband 904 remains in contact with the wrist and hand as the patient moves the wrist and hand. The resilient material of wristband 904, in one embodiment presses stimulation electrodes 1110 against the skin of the wrist and the skin adjacent the thumb. In some embodiments, pressure exerted by the resilient material of wristband 904 helps to support the wrist. Ends 1112 and 1114 of wristband 904 are selectively fastenable to each other using hook-and-loop material, such as VELCRO, straps and buckles, snaps, or the like, for securing wristband 904 around the wrist. In one embodiment, wristband 904 includes an aperture 1116 for receiving the thumb, as shown in FIG. 9.

In one embodiment, elbow-band 902 includes stimulation electrodes 1000, as shown in FIG. 10. Stimulation electrodes 1000 are selectively attachable, in one embodiment, to the interior of elbow-band 902 using snaps, straps and buckles, hook-and-loop material, such as VELCRO or the like. In some embodiments, stimulation electrodes 1000 include conductive electrolytes in the form of fluids, gels, a flexible conductive fabric or material, or the like for electrically coupling stimulation electrodes 1000 to the skin adjacent the elbow.

In another embodiment, elbow-band 902 is of a resilient material so that elbow-band 902 remains in contact with the skin adjacent to the elbow as patient moves. The resilient material of elbow-band 902, in one embodiment, presses stimulation electrodes 1000 against the skin adjacent to the elbow. In some embodiments, pressure exerted by the resilient material of elbow-band 902 helps to support the elbow. Ends 1002 and 1004 of elbow-band 902 are selectively fastenable to each other using hook-and-loop material, such as VELCRO, straps and buckles, snaps or the like, for securing elbow-band 902 around the elbow. In one embodiment, elbow-band 902 includes an aperture 1006 for receiving the elbow, as shown in FIG. 9.

In other embodiments, remote stimulator and sensor device 908 is connected to a stimulation electrode 910 and a common return electrode 912 that are electrically coupled to the shoulder, as shown in FIG. 9, using a conductive adhesive gel. This gel performs a dual function by both electrically coupling stimulation electrode 910 and common return electrode 912 to the shoulder and adhering stimulation electrode 910 and common return electrode 912 to the shoulder. In one example, stimulation electrode 910 and common return electrode 912 are electrically coupled to the shoulder using the various techniques for electrically coupling electrodes to skin described in copending application U.S. Ser. No. 09/659,351, entitled *Adaptive Stimulator for Relief of Symptoms of Neurological Disorders*, filed on Sep. 12, 2000.

Common return electrode 912 provides the return path for each of stimulation electrodes 910, 1000, and 1110. In one embodiment, common return electrode 912 functions as described above for common return electrode 520. Each of stimulation electrodes 910, 1000, and 1110 and common return electrode 912 are connected remote stimulator and sensor device 908. In one embodiment, remote stimulator and sensor device 908 includes an integral accelerometer, e.g., a three-axis accelerometer, configurable to provide information to remote stimulator and sensor device 508 on arm motion and/or to support adaptive modification of stimulation signals supplied to stimulation electrodes 910, 1000, and 1110. In one example, stimulation electrodes 910, 1000, and 1110 and common return electrode 912 are as described in copending application U.S. Ser. No. 09/659, 351, entitled *Adaptive Stimulator for Relief of Symptoms of Neurological Disorders*, filed on Sep. 12, 2000.

Figure 12:
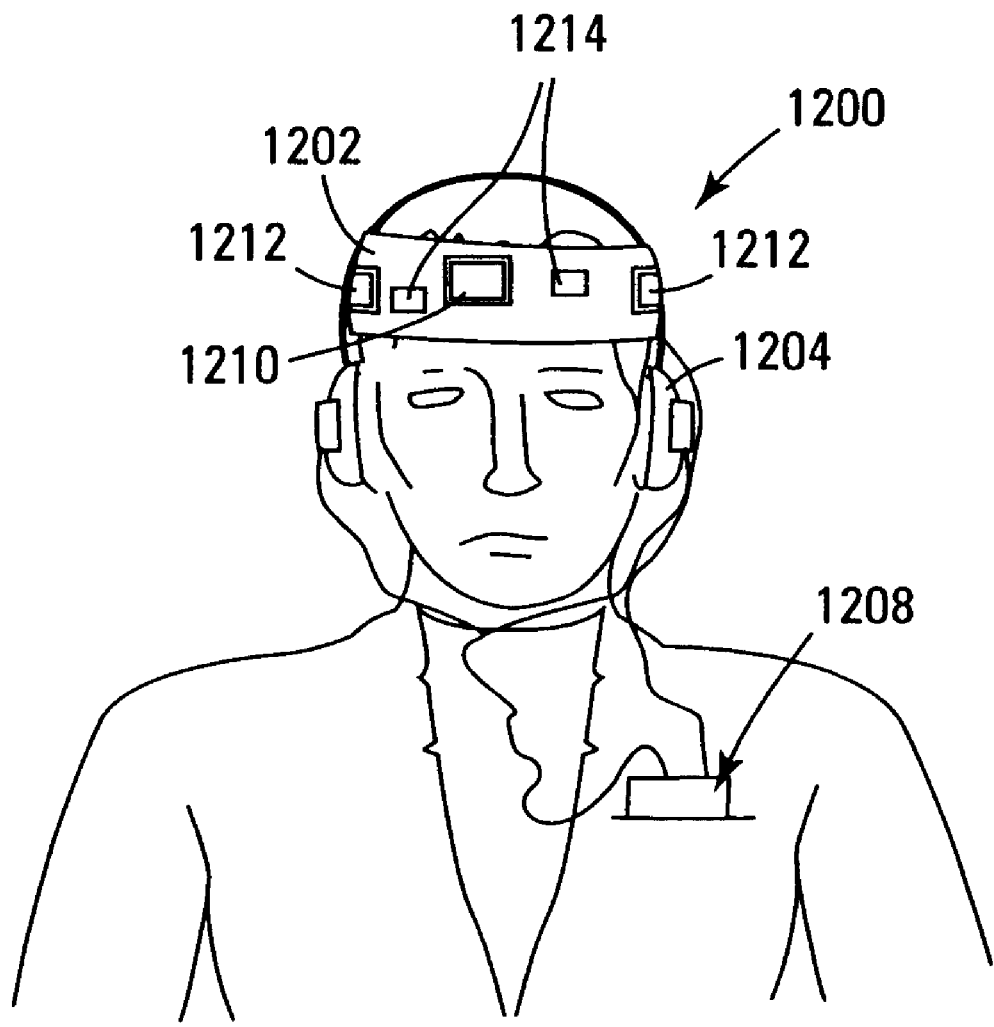
FIG. 12 is an embodiment of a movement timing stimulator for head stimulation according to the teachings of the present invention.

FIG. 12 illustrates an embodiment of a movement timing stimulator 1200. Movement timing stimulator 1200 includes a headband 1202 and headphones 1204 connected to a remote stimulator and sensor device 1208 placeable, for example, in a garment pocket, e.g., shirt, coat, etc., of a patient. In one embodiment, remote stimulator and sensor device 1208 is one of two remote stimulator and sensor devices, e.g., sensor devices $208_1$ to $208_2$, of a movement timing stimulator, e.g., movement timing stimulator 200, that intercommunicate via a remote stimulation interface (RSI), e.g., remote stimulation interface 210. In another embodiment, remote stimulator and sensor device 1208 intercommunicates with remote stimulator and sensor device 508 or remote stimulator and sensor device 908. In other embodiments, a master controller, e.g., master controller 100 or 400, of a movement timing stimulator, e.g., movement timing stimulator 100, replaces remote stimulator and sensor device 1208. In one embodiment, the movement timing stimulator includes remote stimulator and sensor device 508 and remote stimulator and sensor device 908. In another embodiment, remote stimulator and sensor device 1208 is as described above for remote stimulator and sensor device 300.

In one embodiment, headphones 1204 are described as above for headphones 328 or headphones 408. Headband 1202 includes inclination sensors 1210 and 1212. When the head drops or tilts to one side, inclination sensors 1210 and 1212 send sensory signals to remote stimulator and sensor device 1208. Remote stimulator and sensor device 1208 in turn transmits a signal that produces an aural timing cue, as described above, in headphones 1204 instructing the patient to position the head in a normal position. In one embodiment, remote stimulator and sensor device 1208 includes visual indicators, such as visual indicators 336 or 412, perceivable by the patient's peripheral vision. In another embodiment, headband 1202 includes one or more stimulation electrodes, e.g., stimulation electrodes 1214, for providing cutaneous stimulation to the head for instructing the patient to position the head in a normal position.

Conclusion

Embodiments of the present invention have been described. The embodiments provide movement-timing stimulators that aid in the relief of the symptoms of neurological movement disorders by providing sensing and stimulation at various locations of the body of a living subject.

Although specific embodiments have been illustrated and described in this specification, it will be appreciated by those of ordinary skill in the art that any arrangement that is calculated to achieve the same purpose may be substituted for the specific embodiment shown. This application is intended to cover any adaptations or variations of the present invention. For example, although this technology is primarily being developed to relieve symptoms of neurological movement disorders, it has potential for application in other areas. These include symptomatic relief for other disorders, such as, Huntington's disease and rehabilitation therapy for neurological damage. Other applications may include incorporation into flight suits to prevent spatial disorientation of aircrew undergoing high acceleration maneuvers and potential for relieving symptoms of motion sickness.

What is claimed is:

1. A movement timing device for cueing a patient exhibiting one or more symptoms of Parkinson's disease, comprising:
   a control unit;
   a stimulator coupled to an output of to control unit, wherein to stimulator is adapted to provide external stimulation cues to an area of the body of a living subject when impaired voluntary movement is determined;
   a sensor coupled to the control unit and adapted to be disposed external to the body, wherein the sensor is adapted to respond to a physical stimulus and provide input to the control unit; and
   wherein the stimulator is adapted to selectively provide at least one of a dual-polarity signal for providing cutaneous stimulation cues, a phased signal for providing surround sound aural stimulation cues, and a signal for providing visual stimulation cues transmitted to the stimulator by the control unit, wherein the signals cue the patient to make a response.

2. The movement timing device of claim 1, wherein the control unit is selectively coupled to a remote processing unit by an encoded wireless link.

3. The movement timing device of claim 1, wherein the stimulator comprises a visual indicator for providing visual stimulation cues.

4. The movement timing device of claim 1, wherein the stimulator comprises a stimulation electrode for providing cutaneous stimulation cues.

5. The movement timing device of claim 1, wherein the stimulator comprises headphones for providing aural stimulation cues.

6. The movement timing device of claim 1, wherein the sensor comprises at least one of a pressure sensor, an accelerometer, and an inclination sensor.

7. The movement timing device of claim 1, wherein the control unit is adapted to be disposed on one of an ankle or a wrist of a user.

8. The movement timing device of claim 1, wherein the control unit comprises a pair of control units communicatively coupled to each other.

9. The movement timing device of claim 8, wherein one of the pair of control units controls the other of the pair of control units.

10. The movement timing device of claim 8, wherein one of the pair of control units is randomly selected to control the other of the pair of control units.

11. The movement timing device of claim 1, wherein the control unit comprises a plurality of control units communicatively coupled to a master controller for controlling each of the plurality of control units.

12. The movement timing device of claim 1, wherein the control unit is programmed using a configuration controller.

13. The movement timing device of claim 12, wherein the configuration controller comprises a wearable computer.

14. The movement timing device of claim 1, wherein the stimulator is adapted to provide stimulation cues to at least one of the head, the thumb, the wrist, the ankle, the foot, the elbow, the shoulder, and the knee.

15. The movement timing device of claim 1, wherein the sensor is adapted to monitor physical parameters at least one of the wrist, the ankle, the fool, and the head.

16. A movement timing device for cueing a patient exhibiting one or more symptoms of Parkinson's disease, comprising:
  a control unit;
  a stimulation electrode coupled to an output of the control unit, wherein the stimulation electrode is adapted to provide external stimulation cues to an area of the body of a living subject;
  a sensor coupled to the control unit and adapted to be disposed external to the body, wherein the sensor is adapted to respond to a physical stimulus and provide input to the control unit;
  wherein the stimulation electrode is adapted to selectively provide stimulation cues in response to the control unit; and
  wherein the control unit is selectively coupled to a remote processing unit by an encoded wireless link.

17. The movement timing device of claim 16, further comprising a visual indicator for providing visual stimulation cues.

18. The movement timing device of claim 16, further comprising headphones connected to the control unit for providing a surround sound aural cue.

19. A movement timing device for cueing a patient exhibiting one or more symptoms of Parkinson's disease, comprising:
  a control unit;
  a stimulation electrode coupled to an output of the control unit, wherein the stimulation electrode is adapted to provide external stimulation cues to an area of the body of a living subject when impaired voluntary movement is determined;
  a visual indicator coupled to an output of the control unit;
  a sensor coupled to the control unit and adapted to be disposed external to the body, wherein the sensor is adapted to respond to a physical stimulus and provide input to the control unit; and
  wherein the stimulation electrode and the visual indicator are respectively adapted to selectively provide cutaneous stimulation cues and visual stimulation cues in response to the control unit to cue the patient to make a response.

20. The movement timing device of claim 19, further comprising headphones connected to the control unit for providing a surround sound aural cue.

21. A movement timing device for cueing a patient exhibiting one or more symptoms of Parkinson's disease, comprising
  a wristband;
  a first stimulation electrode disposed on an interior of the wristband for cutaneous stimulation of a wrist area of a user when impaired voluntary movement is determined;
  an elbow-band;
  a second stimulation electrode disposed on an interior of the elbow-band for cutaneous stimulation of an elbow area of the user when the impaired voluntary movement is determined;
  wherein the cutaneous stimulation provides external cues to the patient to make a response;
  a control unit secured to the wristband, an output of the control unit is electrically connected to the first and second stimulation electrodes;
  a sensor electrically connected to the control unit and adapted to be disposed external to the body, wherein the sensor is adapted to respond to a physical stimulus and provide input to the control unit; and
  wherein the first and second stimulation electrodes are adapted to selectively provide cutaneous stimulation cues in response to the sensor input to the control unit.

22. The movement timing device of claim 21, wherein the first stimulation electrode comprises a pair of first stimulation electrodes for respectively providing external stimulation cues to a wrist and a thumb of the user.

23. The movement timing device of claim 21, further comprising a third stimulation electrode electrically connected to the control unit for providing cutaneous stimulation cues to a shoulder area of the user in response to the sensor input to the control unit.

24. The stimulator of claim 21, further comprising a common return electrode electrically connected to a shoulder of the user and to the control unit.

25. The stimulator of claim 21, wherein the sensor comprises an accelerometer.

26. A movement timing device for cueing a patient exhibiting one or more symptoms of Parkinson's disease, comprising
  an ankle-band;
  a first stimulation electrode disposed on an interior of the ankle-band wherein the first stimulation electrode is adapted to provide cutaneous stimulation cues to an ankle area of a user;
  a knee-band;
  a second stimulation electrode disposed on an interior of the knee-band wherein the second stimulation electrode is adapted to provide cutaneous stimulation cues to a knee area of the user;
  a control unit secured to the ankle-band, an output of the control unit is electrically connected to the first and second stimulation electrodes;

a sensor electrically connected to the control unit and adapted to be disposed external to the body, wherein the sensor is adapted to respond to a physical stimulus and provide input to the control unit; and wherein the first and second stimulation electrodes are adapted to selectively provide the cutaneous stimulation cues in response to the sensor input to the control unit.

27. The movement timing device of claim 26, wherein the second stimulation electrode comprises a common return electrode.

28. The movement timing device of claim 26, further comprising a sock attached to the ankle-band.

29. The movement timing device of claim 28, further comprising a third stimulation electrode electrically connected to the control unit and disposed on an interior of the sock for cutaneous stimulation of a foot of the user in response to the sensor input to the control unit.

30. The movement timing device of claim 26, wherein the sensor comprises an accelerometer.

31. The movement timing device of claim 26, wherein the sensor comprises a pressure sensor.

32. The movement timing device of claim 31, wherein the pressure sensor is disposed on a shoe insert.

33. A stimulation method for relieving of symptoms of Parkinson's disease, comprising:

receiving an input signal, the input signal comprising a sensory signal based on a physical stimulus;

monitoring the input signal;

selectively generating a stimulation signal when the input signal meets defined criteria, wherein the stimulation signal comprises at least one of a dual-polarity signal for providing cutaneous stimulation cues, a phased signal for providing surround sound aural stimulation cues, and a signal for providing visual stimulation cues;

transmitting the stimulation signal to an area on the exterior of the body of a living subject; and cueing the subject to make a response.

34. The stimulation method of claim 33, wherein receiving the input signal comprises receiving the sensory signal from at least one of an accelerometer, an inclination sensor, and a pressure sensor.

35. The stimulation method of claim 33, wherein receiving the input signal comprises receiving the sensory signal from a sensor disposed on at least one of the wrist, the ankle, the foot, and the head.

36. The stimulation method of claim 33, wherein transmitting the stimulation signal comprises transmitting the stimulation signal to at least one of the head, the thumb, the wrist, the ankle, the foot, the elbow, the shoulder, and the knee.

37. The stimulation method of claim 33, wherein receiving the input signal comprises selectively receiving a sensory signal at each of a pair of control units and transmitting the sensory signal received at one of the pair of control units to the other of the pair of control units.

38. The stimulation method of claim 37, further comprising selecting the other of the pair of control units as a master controller for controlling both of the pair of control units using an arbitration scheme.

39. The stimulation method of claim 38, wherein monitoring the input sensory signal comprises monitoring the sensory signal received at each of the pair of control units at the master controller.

40. The stimulation method of claim 33, wherein receiving the input signal comprises receiving an operator control signal.

41. The stimulation method of claim 40, further comprising transmitting the operator control signal from a configuration controller.

42. The stimulation method of claim 33, further comprising programming a control unit for receiving the input signal and generating the stimulation signal using a configuration controller.

43. The stimulation method of claim 33, further comprising wirelessly transmitting encoded information about the input signals and the stimulation signals to a remote processing unit over an encoded wireless link.

44. The stimulation method of claim 33, further comprising wirelessly transmitting encoded information from a remote processing unit over an encoded wireless link for adjusting the defined criteria.

45. The stimulation method of claim 33, wherein generating the stimulation signal comprises adjusting frequency, pulse width, waveform shape, and amplitude of the stimulation signal based on the input signal.

46. The stimulation method of claim 33, wherein receiving the input signal comprises selectively receiving a sensory signal at each of a plurality of control units and transmitting the sensory signal received at each of the plurality of control units to a master controller for controlling each of the plurality of control units.

47. The stimulation method of claim 33, wherein monitoring the input signal comprises monitoring a sensory signal received at each of a plurality of control units at a master controller for controlling each of the plurality of control units.

48. The stimulation method of claim 33, wherein selectively generating the stimulation signal comprises a master controller selectively instructing each of a plurality of control units to respectively generate a stimulation signal.

49. The stimulation method of claim 33, further comprising comparing a first gait to a second gait.

50. The stimulation method of claim 49, wherein receiving the input signal comprises receiving a sensory signal comprising information on the first gait.

51. The stimulation method of claim 49, wherein selectively generating the stimulation signal comprises generating a stimulation signal for emphasizing the second gait.

* * * * *

UNITED STATES PATENT AND TRADEMARK OFFICE
CERTIFICATE OF CORRECTION

PATENT NO.        : 6,788,976 B2  
APPLICATION NO.   : 10/005458  
DATED             : September 7, 2004  
INVENTOR(S)       : Gesotti Page 1 of 1

It is certified that error appears in the above-identified patent and that said Letters Patent is hereby corrected as shown below:

At Column 12, Claim 1 line 43, please replace "of to control" with --of the control--; line 44, please replace "wherein to simulator" with --wherein the simulator--

At Column 13, Claim 15 line 33, please replace "fool" with --foot--

Signed and Sealed this

First Day of April, 2008

JON W. DUDAS  
*Director of the United States Patent and Trademark Office*